United States Patent
Korman

(10) Patent No.: US 8,743,355 B2
(45) Date of Patent: Jun. 3, 2014

(54) SIMPLE SUGAR CONCENTRATION SENSOR AND METHOD

(71) Applicant: Valentin Korman, Huntsville, AL (US)

(72) Inventor: Valentin Korman, Huntsville, AL (US)

(73) Assignee: K Sciences GP, LLC, San Antonio, TX (US)

( * ) Notice: Subject to any disclaimer, the term of this patent is extended or adjusted under 35 U.S.C. 154(b) by 0 days.

(21) Appl. No.: 13/950,054

(22) Filed: Jul. 24, 2013

(65) Prior Publication Data
US 2014/0104596 A1   Apr. 17, 2014

Related U.S. Application Data

(60) Provisional application No. 61/714,731, filed on Oct. 16, 2012.

(51) Int. Cl.
G01N 33/48 (2006.01)

(52) U.S. Cl.
USPC .......................................................... 356/39

(58) Field of Classification Search
USPC .................................................. 356/39, 364
See application file for complete search history.

(56) References Cited

U.S. PATENT DOCUMENTS

| | | | |
|---|---|---|---|
| 3,724,957 A | 4/1973 | Tamate et al. | |
| 4,014,321 A | 3/1977 | March | |
| 4,699,514 A | 10/1987 | Schmidt et al. | |
| 4,901,728 A * | 2/1990 | Hutchison | 600/316 |
| 5,009,230 A * | 4/1991 | Hutchinson | 600/316 |
| 5,383,452 A * | 1/1995 | Buchert | 600/347 |
| 5,477,327 A * | 12/1995 | Bergman | 356/367 |
| 5,896,198 A | 4/1999 | Chou | |
| 6,016,435 A | 1/2000 | Maruo | |
| 6,370,407 B1 | 4/2002 | Kroeger et al. | |
| 6,567,678 B1 | 5/2003 | Oosta | |
| 6,615,061 B1 | 9/2003 | Khalil | |
| 6,708,048 B1 | 3/2004 | Chance | |
| 6,775,564 B1 | 8/2004 | Peters | |
| 7,245,952 B2 | 7/2007 | Cameron | |
| 7,248,905 B2 | 7/2007 | Fukuda et al. | |
| 7,299,079 B2 | 11/2007 | Rebec | |
| 7,801,581 B2 | 9/2010 | Diab | |
| 8,180,422 B2 | 5/2012 | Rebec | |
| 8,452,360 B2 | 5/2013 | Mandelis | |

* cited by examiner

*Primary Examiner* — Roy M Punnoose

(57) ABSTRACT

A glucose sensor comprising an optical energy source having an emitter with an emission pattern; a first polarizer intersecting the emission pattern; a second polarizer spaced a distance from the first polarizer and intersecting the emission pattern, the second polarizer rotated relative to the first polarizer by a first rotational amount Θ; a first optical detector intersecting the emission pattern; a second optical detector positioned proximal to the second polarizer, the first polarizer and the second polarizer being positioned between the optical energy source and the second optical detector, the second optical detector intersecting the emission pattern; a compensating circuit coupled to the second optical detector; and a subtractor circuit coupled to the compensating circuit and the first optical detector.

19 Claims, 9 Drawing Sheets

US 8,743,355 B2

SIMPLE SUGAR CONCENTRATION SENSOR AND METHOD

CROSS-REFERENCES TO RELATED APPLICATIONS

This original nonprovisional application claims the benefit of U.S. provisional application ser. No. 61/714,731, filed Oct. 16, 2012, which is incorporated by reference herein.

STATEMENT REGARDING FEDERALLY-SPONSORED RESEARCH OR DEVELOPMENT

Not applicable.

BACKGROUND OF THE INVENTION

1. Field of the Invention

The present invention relates to monitoring of simple sugar (or monosaccharide) content within a fluid. More specifically, the invention uses an optical energy source in combination with polarizers to determine the change in a sugar level (e.g., glucose) of a subject fluid relative to a baseline concentration, such as blood.

2. Description of the Related Art

Simple sugar changes the polarization of the optical energy passing through it according to the equation $\Theta = \alpha \times L \times C$, where L is the travel length of the energy through the fluid in which the sugar is concentrated, C is the sugar concentration, and $\alpha$ is a constant that depends on the type of sugar, wavelength of the energy, and the fluid. If L and $\alpha$ are known, by measuring the change in polarization of energy passing through a sugar-containing fluid relative to a baseline measurement, the sugar concentration of the fluid can be derived.

This principal may be used, for example, to non-invasively determine the glucose concentration of human blood. Normal blood has a non-zero glucose concentration C, which causes a change in polarization for energy passing through the blood. For a glucose concentration of 70 mg/dL and an $\alpha = 45.62$ ($\times 10^{-6}$) degrees/mm/(mg/dL), energy of wavelength 633 nm and a 3.0 mm path length will have a rotation $\Theta$ of 0.00958 degrees. Measuring the change in rotation caused by the sugar allows derivation of the current sugar concentration.

SUMMARY OF THE INVENTION

The present invention may be used to monitor sugar (e.g., glucose) in a fluid, and provides numerous advantages over traditional techniques that rely on a standard polarization analyzer, which requires actively moving parts and angular resolution precision to 0.01 degrees. First, the present invention is non-invasive, which lowers the risk of contamination. Second, the present invention may provide an ability to stream real-time, continuous data. Third, the present invention provides a low operating cost.

The invention includes an optical energy source having an emitter with an emission pattern; a first polarizer intersecting the emission pattern; a second polarizer spaced a distance from the first polarizer and intersecting the emission pattern, the second polarizer rotated relative to the first polarizer by a first rotational amount $\Theta$; a first optical detector intersecting the emission pattern; a second optical detector positioned proximal to the second polarizer, the first polarizer and the second polarizer being positioned between the optical energy source and the second optical detector, the second optical detector intersecting the emission pattern; a compensating circuit coupled to the second optical detector; and a subtractor circuit coupled to the compensating circuit and the first optical detector.

DESCRIPTION OF THE VARIOUS EMBODIMENTS

Figure 1:
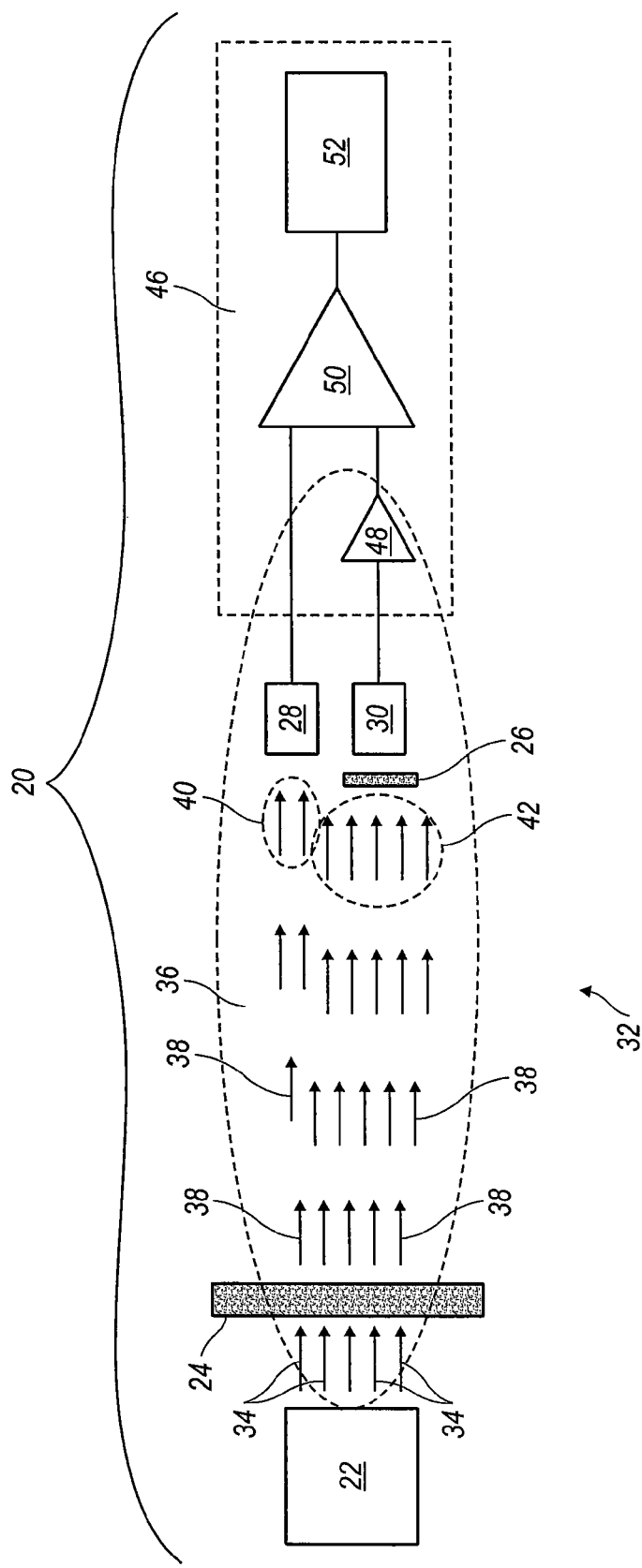
FIG. 1 is a system diagram of an embodiment of the invention.

FIG. 1 shows one embodiment 20 of the invention, which comprises an optical energy source 22, a first polarizer 24, a second polarizer 26 spaced a distance from the first polarizer 24 having a rotation $\Theta$ relative to the first polarizer 24, a first optical energy detector 28, a second optical energy detector 30 collocated with the first detector 28, and a circuit 46. Each of the first and second optical detectors 28, 30 are oriented to receive optical energy passing through a space 32. In the preferred embodiment, the detectors 28, 30 are silicon detectors. As used herein, "collocated" means being positioned adjacent each other so that, all else being equal, light from a common source will enter each of the detectors with approximately equal intensity. In addition, although the embodiment discloses the use of silicon detectors, other types of detectors may be used (e.g., photoresistors).

When actuated, the energy source 22 produces initial optical energy 34 having an emission pattern 36. The energy source 22 is preferably a red light source, such as a red light-emitting diode (LED) or a laser, but may alternatively be near-infrared. Ultimately, the initial optical energy 34 must be of a wavelength that may be affected by the presence of sugar in the subject fluid while also passing through the other vessel in which the fluid is contained.

The first polarizer 24 is positioned proximal to the source 22, such that the initial optical energy 34 passes through the first polarizer 24 and becomes polarized energy 38. The polarized energy 38 traverses the space 32 between the first and second polarizer 24, 26, where a first portion 40 of the polarized energy 38 is detected by a first optical detector 28 and a second portion 42 of the polarized energy 38 passes through a second polarizer 26 to the second optical energy detector 30. Notably, first detector and second detector 28, 30 are collocated, despite the proximity of second polarizer 26 to the second detector 30. Because the space 32 is empty in FIG. 1, the polarized energy 38 passing through the space 32 is not rotated by, for example, the presence of a sugar in a fluid.

Preferably, the first and second polarizers 28, 30 are a linearly-polarized film because such film is inexpensive compared to other available alternatives. Such film, however, is optimal for energy wavelengths in the visible spectrum. Other polarizers may be used, provided that the selected wavelength of the energy source 22 is chosen to optimally correspond. For example, an alternative polarizer may be wire-grid or holographic, which is optimally configured for use in the present invention with energy of near-infrared and infrared wavelengths.

Preferably, the difference in rotation between the polarizers 24, 26 is forty-five degrees (or an integral multiple of forty-five degrees) plus the rotation caused by the baseline. In this optimal case, a change in concentration relative to the baseline at least initially moves along the most linear portion of a sine wave, which makes detecting the change in rotation easier compared to moving further away from where the slope of the wave is 1 and further towards where the slope is 0 (i.e., the crest and troughs of the sine wave). For example, when used with a baseline glucose concentration 100 mg/dL over a length of L, $\Theta$ equals 0.014 degrees. In this case, the rotation between the polarizers should be 45.014 degrees. The greater the change in concentration from the baseline, however, the more non-linear the correlation of the rotation to the change in concentration.

The first and second detectors 28, 30 are electrically coupled to the circuit 46. The circuit 46 has a compensating circuit 48, a subtractor circuit 50, and a gain circuit 52. The first detector 28 is directly coupled to the subtractor circuit 50. The second detector 30 is coupled to the compensating circuit 48, which boosts the gain of the signal produced by the second detector 30 by an amount sufficient to compensate for the loss of intensity attributable to the portion 42 of polarized energy 38 passing through the polarized film and the effects of polarization due to the baseline concentrations in the fluid, but the compensating circuit 48 does not compensate for the loss in intensity resulting from changes in polarization due to the concentration change from some baseline itself. The subtractor circuit 50 produces a signal that is the difference between the signals received from the first and second detectors 28, 30. The gain circuit 52 amplifies the signal to a usable level.

Notably, in alternative embodiments, the compensating circuit 48 may be an attenuator coupled to the first detector 28 to equalize the intensity of the received optical energy, with the objective being that the difference in energy seen by the first detector 28 and the second detector 30 relates to the rotation of the energy rather than its amplitude. Similarly, the subtractor circuit 50 may be replaced by a Wheatstone or similar bridge.

Figure 2:
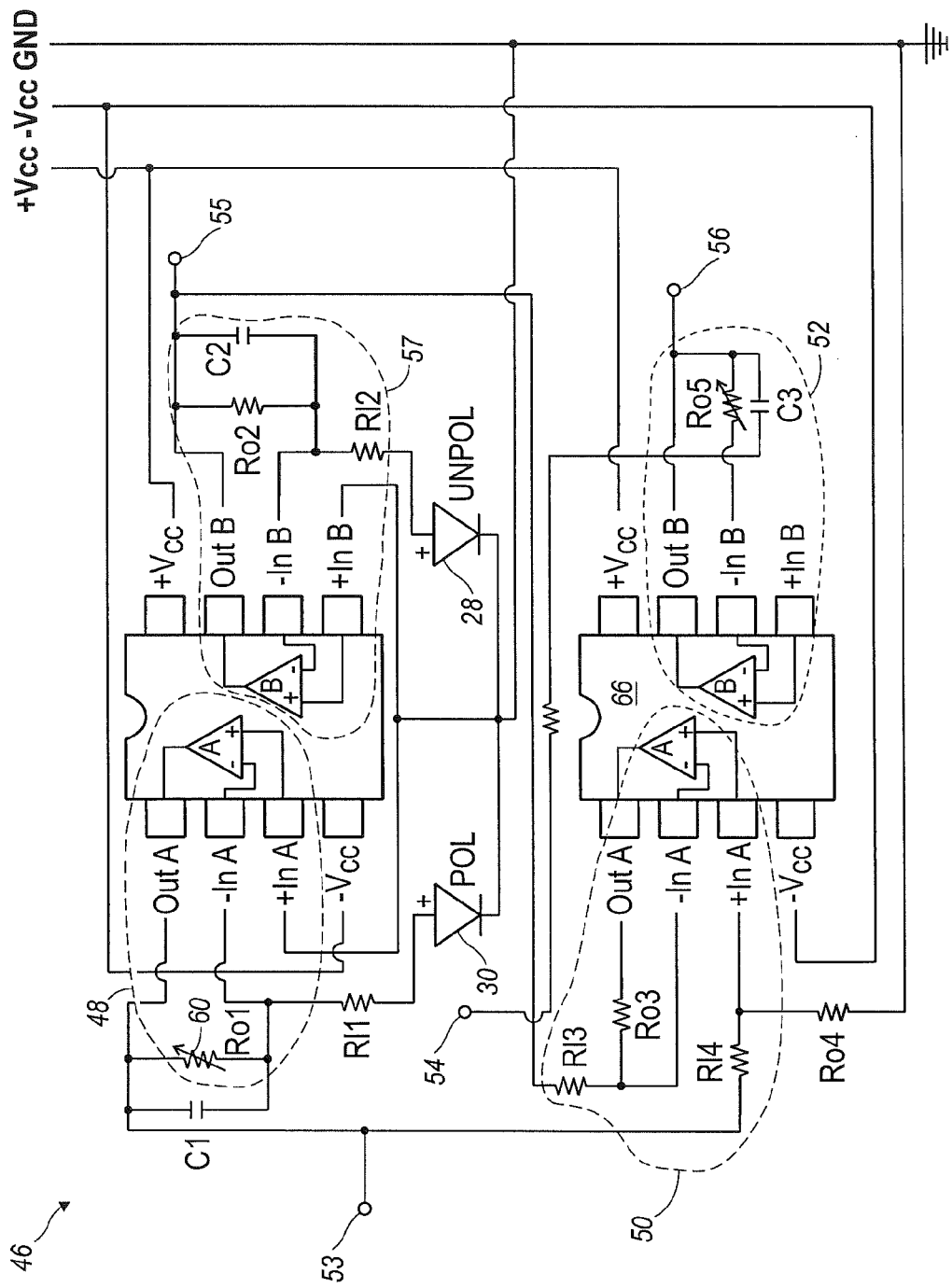
FIG. 2 is a circuit diagram of the circuit described with reference to FIG. 1.

Referring to FIG. 2, the outputs of the first and second detectors 28, 30 are provided to the circuit 46. The circuit 46 comprises the compensating circuit 48 having a potentiometer Ro1, the subtractor circuit 50, first and second 30-Hz low pass filters that included Ro1 and C1, and Ro2 and C2, and the gain circuit 52. The subtractor circuit 50 and the gain circuit 52 incorporate an OPA 211 KP operational amplifier IC 66. The low pass filters reject any noise at the detectors 28, 30. Polarized output 53 and the unpolarized outputs 55 are fed to the subtractor circuit 50, which comprises Ro3, Ro4, R13 and R14. The subtractor circuit output 54 is then provided to the gain circuit 52 comprising Ro5 and C3. The final signal is provided at the gain circuit output 56. The embodiment includes an optional unity gain circuit 57 for phase-matching purposes.

Figure 3:
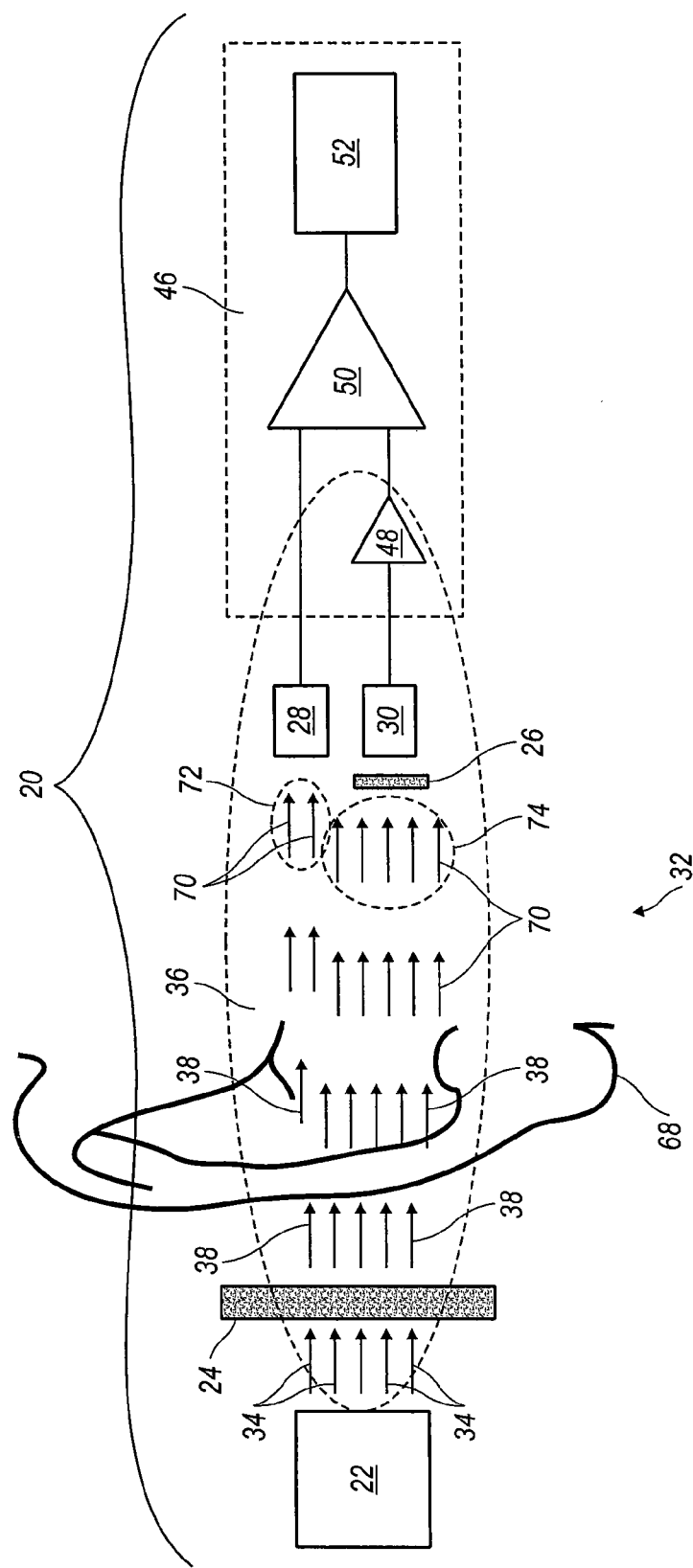
FIG. 3 is the system diagram of FIG. 1 showing the embodiment in use with a human ear.

FIG. 3 shows the embodiment 20 in use with a human ear 68, at least a portion of which occupies the space 32. The preferred orientation of the ear 68 within the space 32 is so that the polarized energy 38 passes through the ear 68 generally parallel to a lateral axis, where L is the distance along the axis of the measured fluid. For most human ears, L is approximately three millimeters of capillary-rich and blood vessel-rich skin.

When actuated, the energy source 22 produces initial optical energy 34 having the emission pattern 36. The initial energy 34 passes through the first polarizer 24, and is of a wavelength to which the non-sugar components of the ear 68 (i.e., skin, blood, tissue, cartilage) are, to at least some extent, transparent.

After passing through the first polarizer 24, the initial energy 34 becomes polarized energy 38. Glucose within the blood in the ear 68, however, will cause a change in polarization of the energy 38 according to $\Theta = \alpha \times L \times C$, causing the rotated energy 70 exiting the ear to have a first rotation $\Theta_1$.

The intensity of a first portion 72 of the rotated energy 70 is detected by the first detector 28. The intensity of a second portion 74 of the rotated energy 70 passes through the second polarizer 26 and is detected by the second detector 30. Each of the first and second detectors 28, 30 produces a signal representative of the received intensity. Because the intensity of the rotated energy 70 received by the second detector 30 is only the intensity of the rotated energy component passing through the second polarizer 26, by measuring the difference in intensities at the detectors 28, 30, the rotation caused by the glucose in the ear 70 can be derived, from which the changed in glucose concentration relative to a baseline can be determined.

To determine the baseline, prior to use, the embodiment 20 is calibrated to a baseline glucose concentration of seventy mg/dL (a "normal" concentration for human blood) by changing the potentiometer 60 to compensate for the difference in intensities of energy received by the first and second detectors 28, 30. Thus, any change in measured rotation represents a change in glucose concentration from some baseline (e.g., 70 mg/dL).

An alternative embodiment of the invention is calibrated to a baseline glucose concentration of 100 mg/dL using wavelength of 650 nm, resulting in a rotation of 45.028 degrees of the second polarizer relative to the first polarizer. This results range of resulting rotation of the baseline plus or minus 0.2 degrees for a glucose concentration of between 30 mg/dL and 300 mg/dL. Thus, a glucose concentration of 30 mg/dL will result in a rotational difference between the detectors of 0.0096 degrees, whereas a glucose concentration of 300 mg/dL will result in a rotational difference of 0.0273 degrees in the opposite direction of the direction of the 30 mg/dL concentration.

There are at least two methods for calibrating the invention. First and preferably, during fabrication of each sensor, a sample control serum or a similar component that would rotate the polarization state a known amount would be inserted in the space. This control would provide a simulated known glucose concentration for use in adjusting the device to the proper calibrated settings. Alternatively, the user/wearer can take an initial reading with the sensor and additionally take a near-simultaneous reading with another glucose sensor (e.g., a blood stick meter). This value from the other sensor would be input into the sensor with user input means such as a knobs, buttons and the like connected to a microcontroller.

Figure 4A:
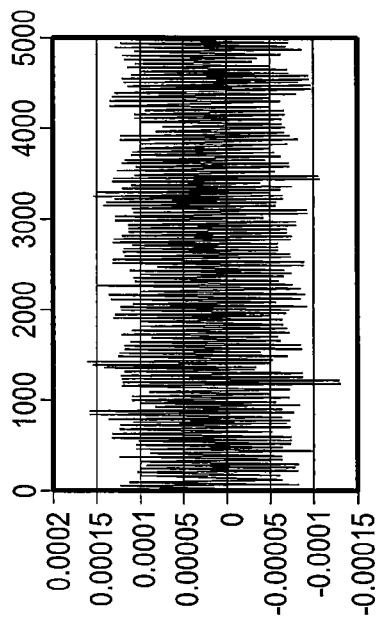
FIG. 4A-4C show actual data from an embodiment of the present invention used to derive sugar concentrations for three separate cases.
Figure 4A:
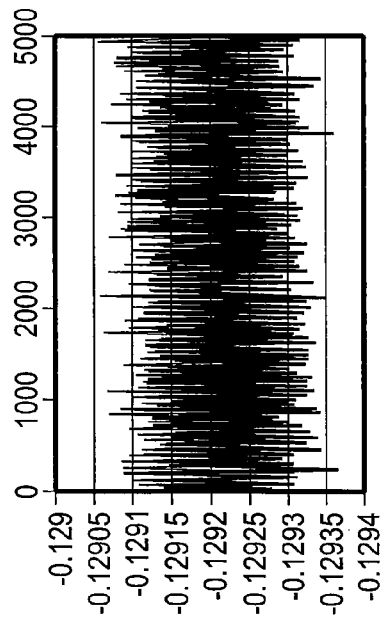
Figure 4A:
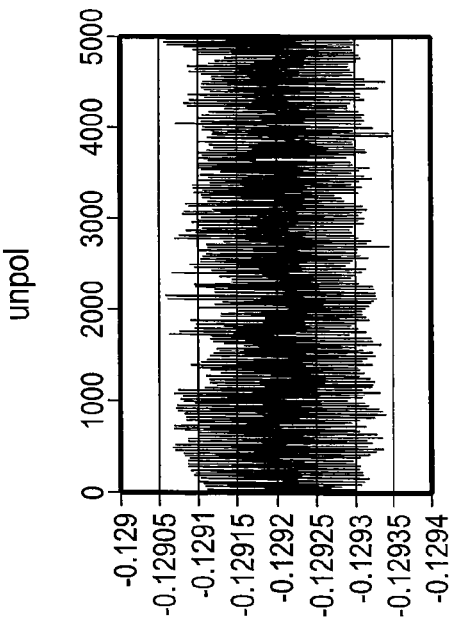
Figure 4B:
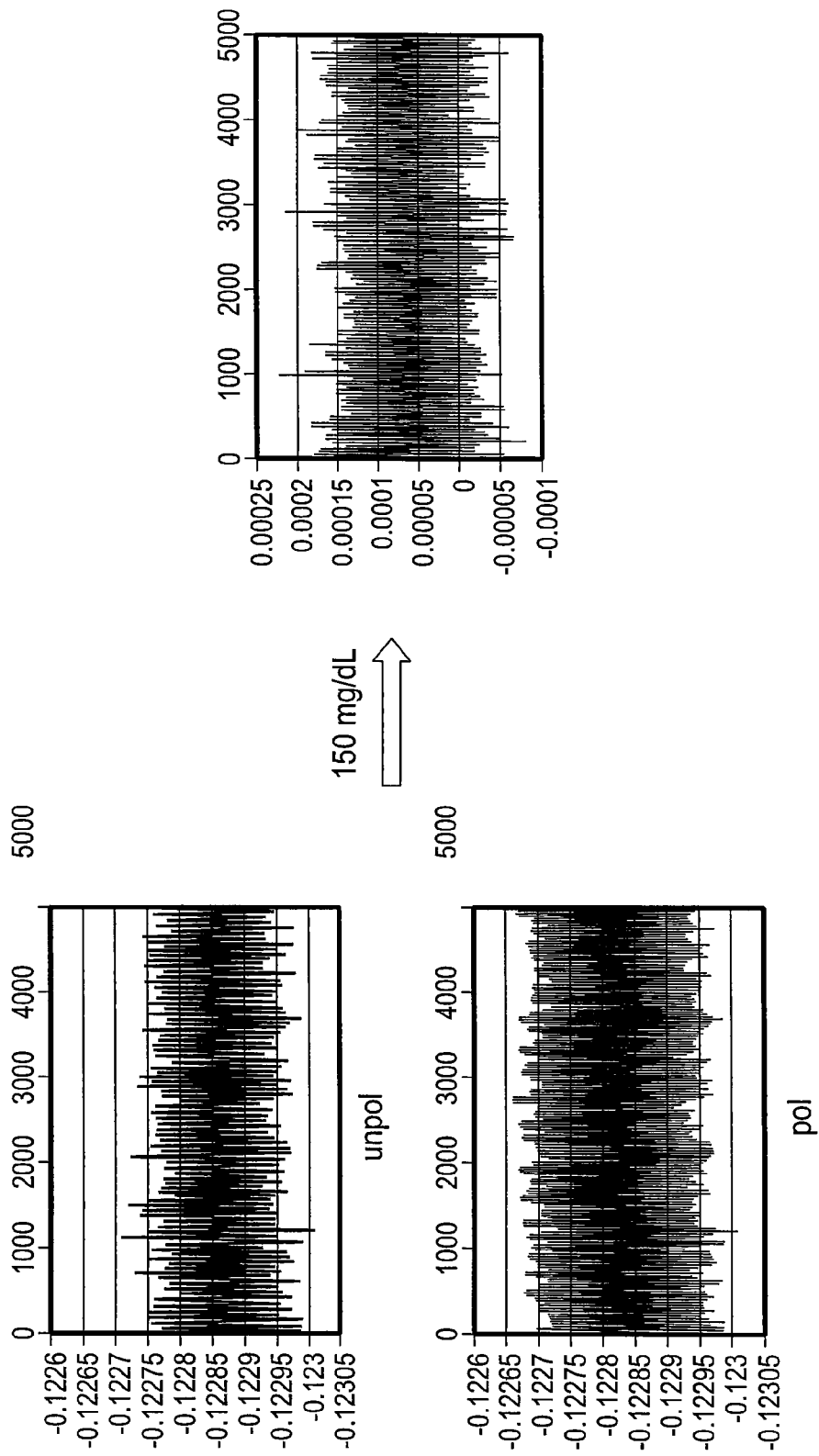
Figure 4C:
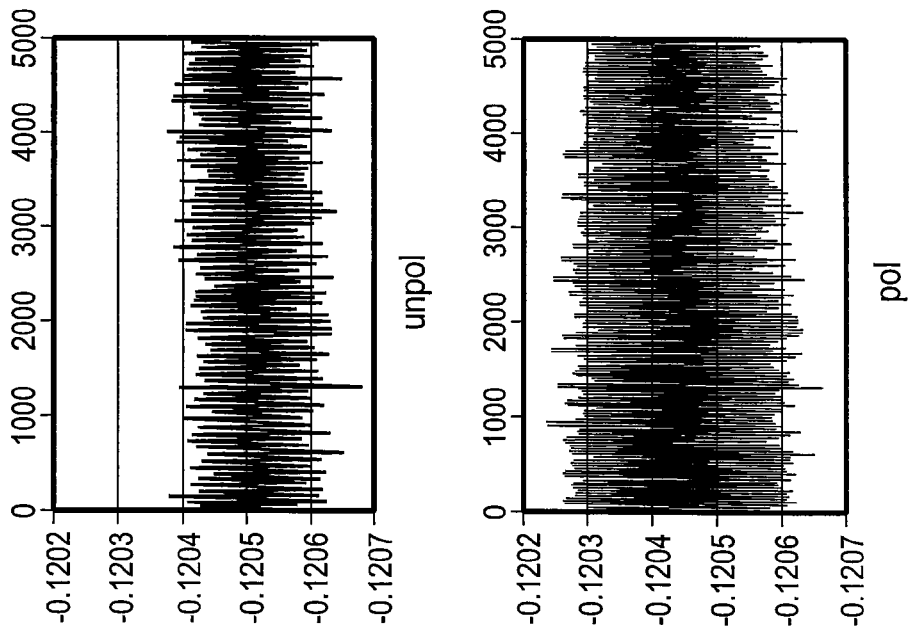

FIGS. 4A-4C shows actual data from an embodiment of the invention used to detect glucose concentrations of 75 mg/dL, 150 mg/dL, and 300 mg/DL. The left side of each example shows actual signals received from the polarized detector 28 and the non-polarized detector 30. The right side of each example shows the output of the subtractor circuit. The embodiment is calibrated for a baseline of 75 mg/dL. In FIG. 4A, the subtractor circuit averages to zero, indicating no change from the baseline. In FIG. 4B, the subtractor circuit averages to approximately 0.00005 Volts. In FIG. 4C, the output of the subtractor circuit averages to approximately 0.0001 Volts, or twice the middle example, which is expected give that the concentration of the bottom example is twice the concentration of shown in FIG. 4B.

Figure 5A:
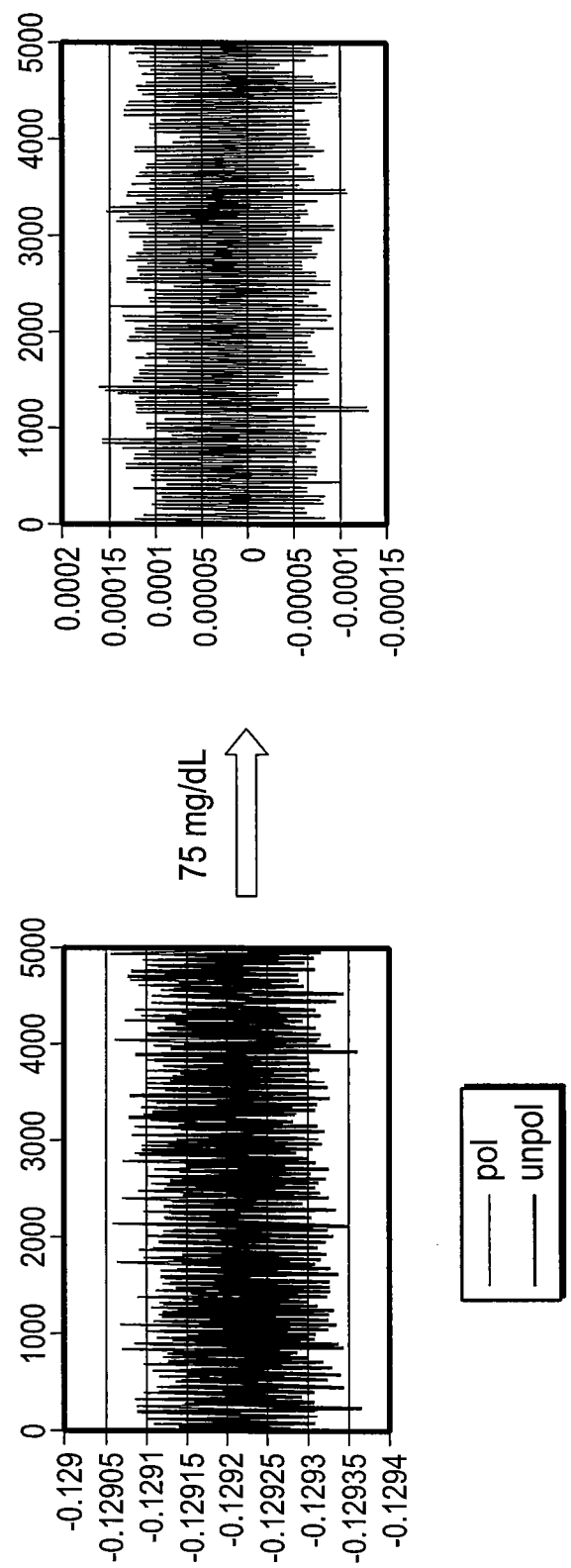
FIG. 5A-5C show the same data shown in FIGS. 4A-4C in a different form, with the unpolarized and polarized waveforms imposed on one another.
Figure 5B:
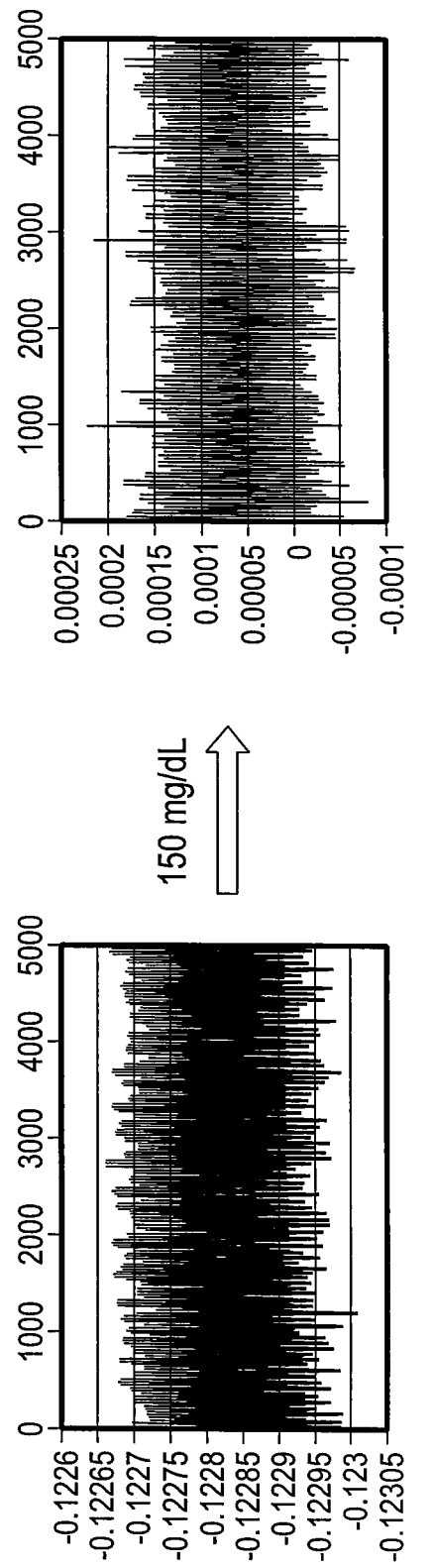
Figure 5C:
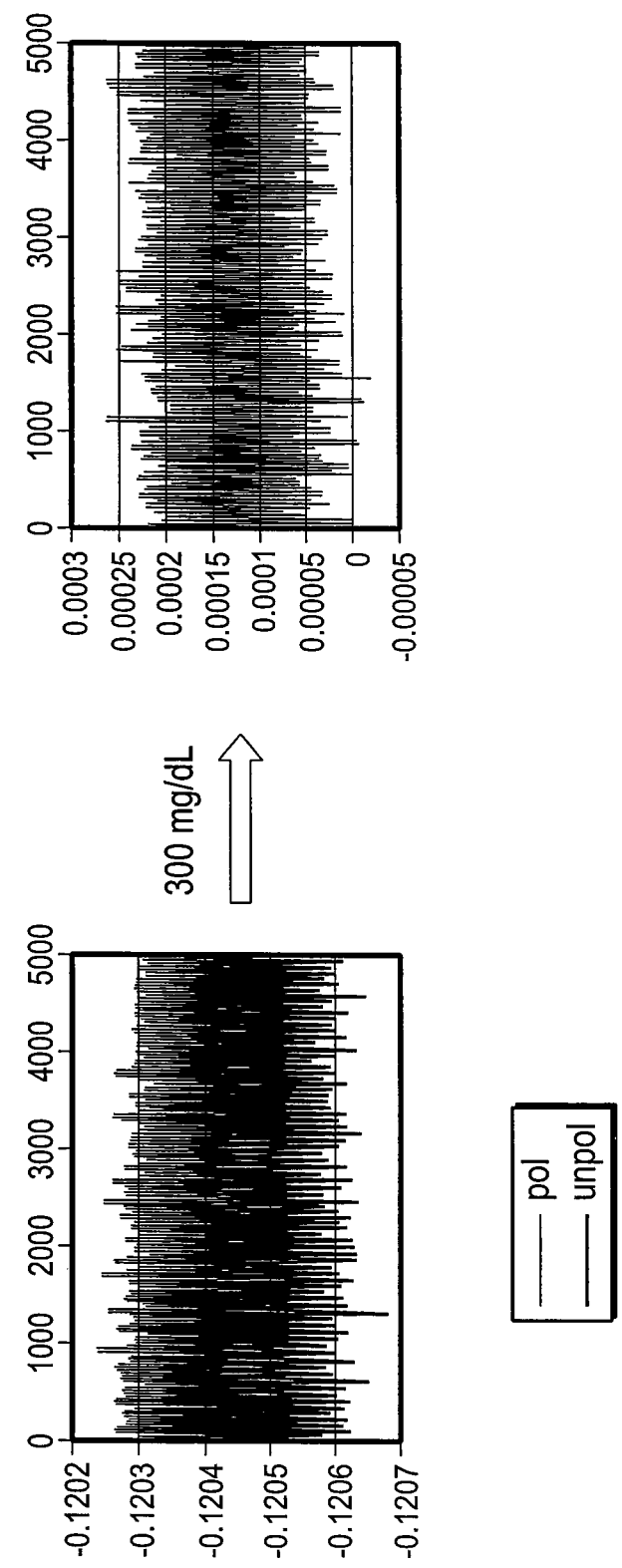

FIGS. 5A-5C show the same data depicted in FIGS. 4A-4C, but with the unpolarized and polarized waveforms on the same graph. FIG. 5A corresponds to the data shown in FIG. 4A. FIG. 5B corresponds to the data shown in FIG. 4B. FIG. 5C corresponds to the data shown in FIG. 4C.

The present disclosure includes preferred or illustrative embodiments in which specific sensors and methods are described. Alternative embodiments of such sensors can be used in carrying out the invention as claimed and such alternative embodiments are limited only by the claims themselves. Other aspects and advantages of the present invention may be obtained from a study of this disclosure and the drawings, along with the appended claims.

I claim:

1. An apparatus for measuring change in sugar concentration in a fluid relative to a baseline concentration, the apparatus comprising:
   a source of optical energy, said source having an emitter with an emission pattern;
   a first optical detector spaced a distance from said source;
   a second optical detector collocated with said first optical detector;
   a plurality of polarizers optically between said source and said detectors, said plurality of polarizers comprising:
      a first polarizer intersecting the emission pattern; and
      a second polarizer rotated relative to the first polarizer by a first rotational amount $\Theta$, spaced a distance from the first polarizer, and proximal to said second optical detector, wherein said first polarizer is optically between said source and said second polarizer;
   a volume of liquid, said volume intersecting said emission pattern and positioned optically between said first polarizer and said second polarizer and optically between said first polarizer and said first detector; and
   at least one circuit coupled to said first optical detector and said second optical detector,
      said at least one circuit comprising:
         a compensating circuit coupled to said second optical detector;
         a subtractor circuit coupled to said compensating circuit and said first optical detector; and
         a gain circuit coupled to said subtractor circuit.

2. The apparatus of claim 1 wherein said at least one circuit further comprises:
   a unity gain circuit coupled to and between said first optical detector and said subtractor circuit.

3. The apparatus of claim 1 wherein $\Theta$ is 45.028 degrees.

4. The apparatus of claim 1 wherein the optical energy source is a near-infrared wavelength optical energy source.

5. The apparatus of claim 1 wherein the optical energy source is a red-wavelength energy source.

6. The apparatus of claim 1 wherein the optical energy source is a LED.

7. The apparatus of claim 1 wherein the optical energy source is a laser.

8. The apparatus of claim 1 wherein the fluid is blood.

9. The apparatus of claim 1 further comprising a form factor wearable around an ear, said form factor housing the optical energy source, the first polarizer, the second polarizer, the first optical detector, and the second optical detector.

10. The apparatus of claim 1 wherein $\Theta$ is between thirty-five and fifty-five degrees (inclusive) of rotation from a baseline rotation caused by a baseline concentration of a simple sugar in a fluid for energy traveling a length L through said fluid.

11. The apparatus of claim 10 wherein $\Theta$ is between forty and fifty degrees (inclusive).

12. The apparatus of claim 11 wherein $\Theta$ is forty-five degrees.

13. The apparatus of claim 1 wherein said plurality of polarizers consists of said first polarizer and said second polarizer.

14. The apparatus of claim 1 wherein said optical energy is unmodulated.

15. A method of detecting an amount of change of sugar concentration in a subject fluid relative to a baseline concentration, the method comprising:
   directing optical energy in a first direction;
   positioning the subject fluid between a first polarizer and a first detector, between said first polarizer and a second polarizer rotated relative to the first polarizer by a first rotational amount $\Theta$, and between said first polarizer and a second detector, wherein said second polarizer is positioned between the first polarizer and said second detector;
   passing the optical energy through the first polarizer to become once-polarized optical energy;
   passing the once-polarized optical energy through the subject fluid to become rotated once-polarized optical energy;
   detecting an intensity of the rotated once-polarized optical energy;
   passing at least a portion of the rotated once-polarized optical energy through the second polarizer to become twice-polarized optical energy;
   detecting the intensity of the twice-polarized optical energy;
   providing a signal representative of a difference between the intensity of the rotated once-polarized optical energy and the intensity of the twice-polarized optical energy; and
   correlating the signal to a sugar concentration.

16. The method of claim 15 wherein the optical energy is red-wavelength optical energy.

17. The method of claim 15 wherein the optical energy is near-infrared optical energy.

18. The method of claim 15 wherein said first optical detector is collocated with said second optical detector.

19. The method of claim 15 wherein the optical energy consists of one unmodulated light wave.

* * * * *